(12) United States Patent
Chen et al.

(10) Patent No.: US 7,267,759 B2
(45) Date of Patent: *Sep. 11, 2007

(54) FRACTIONATING AND FURTHER CRACKING A $C_6$ FRACTION FROM A NAPHTHA FEED FOR PROPYLENE GENERATION

(75) Inventors: Tan Jen Chen, Kingwood, TX (US); Brian Erik Henry, Baton Rouge, LA (US); Paul F Keusenkothen, Houston, TX (US); Philip A. Ruziska, Kingwood, TX (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 449 days.

This patent is subject to a terminal disclaimer.

(21) Appl. No.: 10/760,799

(22) Filed: Jan. 20, 2004

(65) Prior Publication Data

US 2004/0182746 A1    Sep. 23, 2004

Related U.S. Application Data

(60) Provisional application No. 60/451,184, filed on Feb. 28, 2003.

(51) Int. Cl.
*C07C 4/02*     (2006.01)
*C07C 4/06*     (2006.01)

(52) U.S. Cl. .................. 208/113; 208/75; 208/78; 208/80; 208/92; 585/653; 585/300; 585/302; 585/330

(58) Field of Classification Search ............... 585/653, 585/300, 302, 330; 208/75, 78, 80, 92, 113
See application file for complete search history.

(56) References Cited

U.S. PATENT DOCUMENTS

| | | | |
|---|---|---|---|
| 2,426,903 A | 9/1947 | Sweeney | |
| 3,692,667 A | 9/1972 | McKinney et al. | |
| 4,051,013 A | 9/1977 | Strother | 208/78 |
| 4,717,466 A | 1/1988 | Herbst et al. | |
| 5,082,983 A | 1/1992 | Breckenridge et al. | 585/475 |
| 5,087,349 A | 2/1992 | Goelzer et al. | 208/113 |
| 5,264,115 A | 11/1993 | Mauleon et al. | 208/67 |
| 5,358,918 A | 10/1994 | Yukang et al. | 502/67 |
| 5,506,365 A | 4/1996 | Mauleon et al. | 585/329 |
| 5,846,403 A | 12/1998 | Swan et al. | 208/113 |
| 5,888,378 A | 3/1999 | Kowalski | 208/114 |
| 6,069,287 A | 5/2000 | Ladwig et al. | 585/648 |
| 6,080,303 A | 6/2000 | Cao et al. | 208/120.01 |
| 6,090,271 A | 7/2000 | Carpency et al. | 208/113 |
| 6,093,867 A | 7/2000 | Ladwig et al. | 585/648 |
| 6,106,697 A | 8/2000 | Swan et al. | 208/77 |
| 6,118,035 A | 9/2000 | Fung et al. | 585/653 |
| 6,222,087 B1 | 4/2001 | Johnson et al. | 585/651 |
| 6,258,257 B1 | 7/2001 | Swan, III et al. | 208/74 |
| 6,258,990 B1 | 7/2001 | Fung et al. | 585/330 |
| 6,313,366 B1 | 11/2001 | Ladwig et al. | 585/648 |
| 6,315,890 B1 | 11/2001 | Ladwig et al. | 208/67 |
| 6,339,180 B1 | 1/2002 | Ladwig et al. | 585/330 |
| 6,339,181 B1 | 1/2002 | Chen et al. | 585/653 |
| 2001/0025806 A1 | 10/2001 | Steffens et al. | 208/113 |
| 2001/0042700 A1 | 11/2001 | Swan, III et al. | 208/68 |
| 2001/0053868 A1 | 12/2001 | Chester et al. | 585/648 |

FOREIGN PATENT DOCUMENTS

| | | |
|---|---|---|
| BE | 1061116 | 12/2000 |
| DE | 0152356 | 11/1981 |
| DE | 3609653 | 11/1986 |
| EP | 0654523 | 8/1999 |
| EP | 1205530 | 5/2002 |
| EP | 0849347 | 4/2003 |
| FR | 0323297 | 6/1991 |
| JP | 61289049 | 12/1986 |
| WO | WO 00/40672 | 7/2000 |
| WO | WO 01/34727 | 5/2001 |
| WO | WO 01/34729 | 5/2001 |
| WO | WO 01/34730 | 5/2001 |
| WO | WO 01/64763 | 9/2001 |
| WO | WO 01/79383 | 10/2001 |
| WO | WO 01/90278 | 11/2001 |

OTHER PUBLICATIONS

*Canadian Journal of Chem. Eng.* 63(3), 451-461, 1985, (Reference 6, Queen's University, Kingston, Canada) entitled "Catalytic Cracking and Skeletal Isomerization of n-Hexene on SZM-5 Zeolite."

*Chinese Journal of Catalysis* (Cuihua Zuebao), 11(2), 132-137, 1991, (Reference 4, Dalian Inst. of Chem. Phys., Academy Sinica, China) entitled "Studies on the Cracking of 1-Hexene over Pillared Clay Molecular Sieve."

Niccum, P.K., et al.: "Maxofintm: A Novel FCC Process for Maximizing Light Olefins Using a New Generation ZSM-5 Additive." Annual Meeting Mobil Technology Company National Petroleum Refines Association, Niccum, XX, XX, Mar. 1998, pp. 1-1A, XP002927512 the whole document.

Richard J. Quann, Larry A. Green, Samuel A. Tabak, Frederick J. Krambeck, "Chemistry of Olefin Oligomerization over ZSM-5 Catalyst," Ind. Eng. Chem. Res. 1988, 27, 565-570, 1988 American Chemical Society.

*Primary Examiner*—Tam M. Nguyen
(74) *Attorney, Agent, or Firm*—Jeremy J. Kliebert; Bruce M. Bordelon

(57) ABSTRACT

The present invention relates to a process for selectively producing $C_3$ olefins from a catalytically cracked or thermally cracked naphtha stream by fractionating the naphtha feed to obtain a $C_6$ fraction and feeding the $C_6$ fraction either in the riser downstream of the injection point for the reminder of the naphtha feed, in the stripper, and/or in the dilute phase immediately downstream or above the stripper of a process unit.

39 Claims, No Drawings

FRACTIONATING AND FURTHER CRACKING A $C_6$ FRACTION FROM A NAPHTHA FEED FOR PROPYLENE GENERATION

CROSS-REFERENCE TO RELATED APPLICATION

This application claims benefit of U.S. provisional patent application Ser. No. 60/451,184 filed Feb. 28, 2003.

FIELD OF THE INVENTION

The present invention relates to a process for selectively producing $C_3$ olefins from a catalytically cracked or thermally cracked naphtha stream by fractionating the naphtha feed to obtain a $C_6$ fraction and feeding the $C_6$ fraction either in the riser downstream of the injection point for the reminder of the naphtha feed, in the stripper, and/or in the dilute phase immediately downstream or above the stripper of a process unit.

BACKGROUND OF THE INVENTION

The need for low emissions fuels has created an increased demand for light olefins for use in alkylation, oligomerization, MTBE and ETBE synthesis processes. In addition, a low cost supply of light olefins, particularly propylene, continues to be in demand to serve as feedstock for polyolefin, particularly polypropylene production.

Fixed bed processes for light paraffin dehydrogenation have recently attracted renewed interest for increasing olefin production. However, these types of processes typically require relatively large capital investments as well as high operating costs. It is therefore advantageous to increase olefin yield using processes, which require relatively small capital investment. It is particularly advantageous to increase olefin yield in catalytic cracking processes.

U.S. Pat. No. 4,830,728 to Herbst et al. discloses a FCC unit that is operated to maximize olefin production. The FCC unit has two separate risers into which a different feed stream is introduced. The operation of the risers is designed so that a suitable catalyst will act to convert a heavy gas oil in one riser and another suitable catalyst will act to crack a lighter naphtha feed in the other riser. Conditions within the heavy gas oil riser can be modified to maximize either gasoline or olefin production. The primary means of maximizing production of the desired product is by using a catalyst that favors the production of the desired product slate.

U.S. Pat. No. 5,389,232 to Adewuyi et al. describes a FCC process in which the catalyst contains up to 90 wt. % conventional large pore cracking catalyst and an additive containing more than 3.0 wt. % ZSM-5 (a medium pore catalyst) on a pure crystal basis on an amorphous support. The patent indicates that although ZSM-5 increases $C_3$ and $C_4$ olefins, high temperatures degrade the effectiveness of the ZSM-5. Therefore, a temperature of 950° F. to 1100° F. (510° C. to 593° C.) in the base of the riser is quenched with light cycle oil downstream of the base to lower the temperature in the riser 10° F.-100° F. (5.6° C.-55.6° C.). The ZSM-5 and the quench increase the production of $C_3/C_4$ light olefins but there is no appreciable ethylene product.

European Patent Specifications 490,435-B and 372,632-B and European Patent Application 385,538-A describe processes for converting hydrocarbonaceous feedstocks to olefins and gasoline using fixed or moving beds. The catalysts included ZSM-5 in a matrix, which included a large proportion of alumina.

U.S. Pat. No. 5,069,776 teaches a process for the conversion of a hydrocarbonaceous feedstock by contacting the feedstock with a moving bed of a zeolite catalyst comprising a zeolite with a medium pore diameter of 0.3 to 0.7 nm, at a temperature above about 500° C. and at a residence time less than about 10 seconds. Olefins are produced with relatively little saturated gaseous hydrocarbons being formed. Also, U.S. Pat. No. 3,928,172 to Mobil teaches a process for converting hydrocarbonaceous feedstocks wherein olefins are produced by reacting said feedstock in the presence of a ZSM-5 catalyst.

A problem inherent in producing olefin products using FCC units is that the process depends on a specific catalyst balance to maximize production of light olefins while also achieving high conversion of the 650° F.$^+$ feed components to fuel products. In addition, even if a specific catalyst balance can be maintained to maximize overall olefin production relative to fuels, olefin selectivity is generally low due to undesirable side reactions, such as extensive cracking, isomerization, aromatization and hydrogen transfer reactions. Light saturated gases produced from undesirable side reactions result in increased costs to recover the desirable light olefins. Therefore, it is desirable to maximize olefin production in a process that allows a high degree of control over the selectivity of $C_3$ and $C_4$ olefins while producing minimal by-products.

SUMMARY OF THE INVENTION

One embodiment of the present invention is a process for producing increased amounts of propylene from naphtha-boiling-range feedstreams in a process unit comprising at least a reaction zone, a stripping zone, a regeneration zone, and at least one fractionation zone, which process comprises:

(a) fractionating a naphtha-boiling-range feedstream to produce at least a $C_6$-rich fraction and a $C_6$-lean fraction;

(b) injecting at least a portion of said $C_6$-lean fraction into the reaction zone, said reaction zone containing a cracking catalyst comprising at least one molecular sieve having an average pore diameter of less than about 0.7 nm wherein said $C_6$-lean fraction contacts said cracking catalyst under effective conditions thereby resulting in at least spent catalyst particles having carbon deposited thereon and a product stream;

(c) injecting at least a portion of said $C_6$-rich fraction at a place in the process unit selected from: i) downstream of the $C_6$-lean fraction; ii) the stripping zone; and iii) a dilute phase above the stripping zone;

(d) contacting at least a portion of said spent catalyst particles with a stripping gas in the stripping zone under conditions effective at removing at least a portion of any volatiles therefrom thereby resulting in at least stripped spent catalyst particles;

(e) regenerating at least a portion of said stripped spent catalysts in a regeneration zone in the presence of an oxygen-containing gas under conditions effective at burning off at least a portion of said carbon deposited thereon thereby producing at least regenerated catalyst particles;

(f) recycling at least a portion of said regenerated catalyst particles to said reaction zone;

(g) fractionating at least a portion of said product stream of step (b) to produce at least a fraction rich in propylene; and (h) collecting at least a portion of the fraction rich in propylene.

Another embodiment of the present invention provides a process for producing increased amounts of propylene from naphtha-boiling-range feedstreams in a process unit comprising at least a reaction zone, a stripping zone, a regeneration zone, and at least one fractionation zone, which process comprises:

(a) injecting a naphtha-boiling-range feedstream into the reaction zone, said reaction zone containing a cracking catalyst comprising at least one molecular sieve having an average pore diameter of less than about 0.7 nm wherein said $C_6$-lean fraction contacts said cracking catalyst under effective conditions thereby resulting in at least spent catalyst particles having carbon deposited thereon and a product stream;

(b) contacting at least a portion of said spent catalyst particles with a stripping gas in the stripping zone under conditions effective at removing at least a portion of any volatiles therefrom thereby resulting in at least stripped spent catalyst particles;

(c) regenerating at least a portion of said stripped spent catalysts in a regeneration zone in the presence of an oxygen-containing gas under conditions effective at burning off at least a portion of said carbon deposited thereon thereby producing at least regenerated catalyst particles;

(d) recycling at least a portion of said regenerated catalyst particles to said reaction zone;

(e) fractionating at least a portion of said product stream of step (a) to produce at least a fraction rich in propylene, a $C_6$-rich fraction, and a $C_6$-lean fraction; and (f) collecting at least a portion of the fraction rich in propylene and the $C_6$-lean fraction and recycling at least a portion of the $C_6$-rich fraction to a place in the process unit selected from: i) downstream of the $C_6$-lean fraction; ii) the stripping zone; iii) with the $C_6$-lean fraction; and iv) a dilute phase above the stripping zone.

Another embodiment of the present invention provides a process for producing increased amounts of propylene from naphtha-boiling-range feedstreams in a process unit comprising at least a reaction zone, a stripping zone, a regeneration zone, and at least one fractionation zone, which process comprises:

(a) fractionating a naphtha-boiling-range feedstream to produce at least a $C_6$-rich feed fraction and a $C_6$-lean feed fraction;

(b) injecting at least a portion of said $C_6$-lean feed fraction into the reaction zone, said reaction zone containing a cracking catalyst comprising at least one molecular sieve having an average pore diameter of less than about 0.7 nm wherein said $C_6$-lean feed fraction contacts said cracking catalyst under effective conditions thereby resulting in at least spent catalyst particles having carbon deposited thereon and a product stream;

(c) injecting at least a portion of said $C_6$-rich feed fraction into the process unit at a place in the process unit selected from: i) downstream the $C_6$-lean fraction; ii) the stripping zone; and iii) a dilute phase reaction zone;

(d) contacting at least a portion of said spent catalyst particles with a stripping gas in the stripping zone under conditions effective at removing at least a portion of any volatiles therefrom, thereby resulting in at least stripped spent catalyst particles;

(e) regenerating at least a portion of said stripped spent catalysts in a regeneration zone in the presence of an oxygen-containing gas under conditions effective at burning off at least a portion of said carbon deposited thereon;

(f) recycling at least a portion of said regenerated catalyst particles to said reaction zone;

(g) fractionating at least a portion of said product stream of step (b) to produce at least a fraction rich in propylene; a $C_6$-rich product fraction, and $C_6$-lean product fraction; and (h) collecting at least a portion of the propylene and $C_6$-lean product fraction and recycling at least a portion of the $C_6$-rich product fraction to a place in the process unit selected from: i) downstream the $C_6$-lean feed fraction; ii) the stripping zone; and iii) a dilute phase above the stripping zone.

DETAILED DESCRIPTION OF THE INVENTION

While attempts have been made to increase light olefins yields in Fluidized Catalytic Cracking ("FCC") process units, it is preferred that the present invention use its own distinct process unit, as described below, which can receive a naphtha-boiling-range feedstream from any suitable source in the refinery. In the practice of the present invention, the reaction zone of the process unit is operated under process conditions effective at maximizing the $C_2$ to $C_4$ olefins (particularly propylene) selectivity. Thus, the present invention relates to a process for selectively producing $C_3$ olefins from a catalytically cracked or thermally cracked naphtha-boiling-range feedstream. The naphtha boiling range feedstream is further cracked in a process unit comprising a reactor having a riser into which the naphtha feedstream is injected, a reaction zone, a stripping zone, a regeneration zone, and at least one fractionation zone. The reaction zone comprises at least one dynamic catalyst bed. Non-limiting examples of dynamic catalyst beds include fluidized, slurried or ebullating.

Feedstreams which are suitable for use herein are naphtha-boiling-range feedstreams boiling in the range of about 65° F. to about 430° F., preferably from about 65° F. to about 300° F. Non-limiting examples of naphtha-boiling-range feedstreams suitable for use herein include light naphthas or raffinates, containing sufficient amounts of $C_4$-$C_9$ olefins and/or paraffins, $C_4$-$C_9$ fractions from light naphthas or raffinates, catalytic cracked naphtha, coker naphtha, steam cracker pyrolysis gasoline, synthetic chemical streams containing sufficient amounts of $C_4$-$C_9$ olefins and/or paraffins or any other hydrocarbons containing sufficient amounts of $C_4$-$C_9$ olefins and/or paraffins. Feedstreams containing high levels of dienes, sulfur, nitrogen, and oxygenates may be selectively hydrotreated prior to use in the presently disclosed process. However, appropriate feeds with low levels of dienes, sulfur, nitrogen, metal compounds and oxygenates can be processed directly from FCC units, cokers or steam crackers without any pretreatment.

One embodiment of the present invention is practiced by fractionating a naphtha-boiling-range feedstream in a first fractionation zone, thus producing at least a $C_6$-rich fraction and a $C_6$-lean fraction. The $C_6$-rich fraction of the present invention is to be considered that fraction which typically contains at least about 50 wt. %, preferably at least about 60 wt. %, and more preferably at least about 70 wt. % of $C_6$ compounds. At least a portion, preferably substantially all, of the $C_6$-lean fraction is injected into the reaction zone. The injection of the $C_6$-lean fraction is typically achieved by feeding it into a so-called "primary riser". At least a portion, preferably substantially all, of the $C_6$-rich fraction is injected into the process unit at a place in the process unit selected from: i) downstream of the injection of the $C_6$-lean fraction; ii) the stripping zone; and iii) a dilute phase above the stripping zone, wherein "downstream" is in relation to the flow of the $C_6$-lean fraction. Dilute phase, as used herein, is meant to refer to that portion above the stripping zone wherein the catalyst density is substantially lower than the catalyst density in the other portions of the stripping zone. Within the process unit, both the $C_6$-rich fraction and the $C_6$-lean fraction contact hot catalyst particles in the reaction zone under effective conditions that "crack" the respective fractions. The respective fractions contact the hot catalyst under effective conditions including temperatures from about 500° C. to about 650° C., preferably from about 525° C. to about 600° C. The cracking reaction results in the production of at least a product stream and "spent catalyst particles" having deposits of carbon thereon. The product stream resulting from the cracking reaction is separated from the catalyst particles and sent to a second fractionator. At least a portion, preferably substantially all, of the spent catalyst particles pass through a stripping zone where a stripping medium contacts the spent catalyst particles under conditions effective at removing at least a portion of any volatiles from the spent catalyst particles. The stripping medium can be any stripping medium known in the art to be effective at removing volatiles from spent catalyst particles such as, for example, steam. The stripping of the spent catalyst particles produces at least stripped spent catalyst particles that are subsequently regenerated. It should be noted that preferred stripping stages suitable for use herein will have a dilute phase region above the dense phase in the stripper. The stripping zone can be operated in both a counter-current, i.e. the stripping medium contacts the spent catalyst particles from a direction opposite the direction of flow of the spent catalyst particles, or in a co-current fashion. However, it is preferred that the catalyst particles be contacted with the stripping medium in a counter-current fashion. It is also preferred that the stripping zone be operated under low-severity conditions. By "low severity conditions" it is meant those conditions selected to retain a greater fraction of any adsorbed hydrocarbons for heat balance.

As mentioned above, the stripped spent catalyst particles are regenerated. In the regeneration of the stripped catalyst particles, at least a portion, preferably substantially all, of the stripped spent catalyst particles are conducted to a regeneration zone. In the regeneration zone, the stripped spent catalyst particles are regenerated by burning at least a portion of the carbon deposits from the catalyst in the presence of an oxygen-containing gas, preferably air. The regeneration of the spent stripped catalyst particles restores catalyst activity and simultaneously heats the catalyst to a temperature from about 650° C. to about 750° C. Thus, the regeneration zone is operated under conditions effective at burning off at least a portion of the carbon deposits from the spent catalyst particles thus resulting is catalyst particles referred to herein as "regenerated catalyst particles". The hot regenerated catalyst particles are then recycled to the reaction zone to react with fresh naphtha feed.

At least a portion, preferably substantially all, of the product stream from the reaction zone is sent to a fractionation zone where various products are recovered, particularly a $C_3$-rich, i.e. propylene rich, fraction, and optionally a $C_4$-rich fraction, and a $C_6$-rich product fraction and/or a $C_6$-lean product fraction. At least a portion, preferably substantially all, of the $C_3$ (propylene)-rich fraction can then be collected. The $C_3$ fraction and the $C_4$ fraction will typically be rich in olefins. In the practice of the present invention, at least a portion, preferably substantially all, of the $C_6$-rich product fraction can be recycled to various points in the process unit to increase the yield of propylene. For example, it can be recycled to a dilute phase in either the stripper or reaction zone. The dilute phase will typically be above the dense phase of the stripping zone at the lower section of the process unit. The portion of the $C_6$-rich product fraction recycled can also be introduced into the reaction zone by injecting it downstream of the injection point of the naphtha feedstream or the $C_6$-lean feed fraction, this will typically be in the riser portion of the process unit. The portion of the $C_6$-rich product fraction recycled can also be introduced into a second riser if a dual riser process unit is utilized.

Catalysts suitable for use in the practice of the present invention are cracking catalysts that are comprised of at least one molecular sieve having an average pore diameter less than about 0.7 nanometers (nm). The at least one molecular sieve typically comprises from about 10 wt. % to about 50 wt. % of the total fluidized catalyst composition. Molecular sieves suitable for use herein are selected from those materials referred to in the art as zeolites and silicoaluminophosphates (SAPO). It is preferred that the at least one molecular sieve be selected from that class of materials known as zeolites, and more preferred that the zeolite be selected from medium pore zeolites. Medium pore size zeolites that can be used in the practice of the present invention are those described in the "Atlas of Zeolite Structure Types", eds. W. H. Meier and D. H. Olson, Butterworth-Heineman, Third Edition, 1992, which is hereby incorporated by reference. Medium pore size zeolites generally have an average pore diameter less than about 0.7 nm, typically from about 0.5 nm, to about 0.7 nm and include for example, MFI, MFS, MEL, MTW, EUO, MTT, HEU, FER, and TON structure type zeolites (IUPAC Commission of Zeolite Nomenclature). Non-limiting examples of such medium pore size zeolites, include ZSM-5, ZSM-12, ZSM-22, ZSM-23, ZSM-34, ZSM-35, ZSM-38, ZSM-48, ZSM-50, silicalite, and silicalite 2. The most preferred zeolite cracking catalyst used in the presently disclosed process is ZSM-5, which is described in U.S. Pat. Nos. 3,702,886 and 3,770,614. ZSM-11 is described in U.S. Pat. No. 3,709,979; ZSM-12 in U.S. Pat. No. 3,832,449; ZSM-21 and ZSM-38 in U.S. Pat. No. 3,948,758; ZSM-23 in U.S. Pat. No. 4,076,842; and ZSM-35 in U.S. Pat. No. 4,016,245. All of the above patents are incorporated herein by reference. Of particular interest are the medium pore zeolites with a silica to alumina molar ratio of less than about 75:1, preferably less than about 50:1, and more preferably less than about 40:1. The pore diameter, sometimes referred to herein as "effective pore diameter", can be measured using standard adsorption techniques and hydrocarbonaceous compounds of known minimum kinetic diameters. See Breck, Zeolite Molecular Sieves, 1974 and Anderson et al., J. Catalysis 58, 114 (1979), both of which are incorporated herein by reference.

As mentioned above, molecular sieves suitable for use herein also include that class of materials generally known as silicoaluminophosphates (SAPO), such as, for example, SAPO-11, SAPO-34, SAPO-41, and SAPO-42, which are described in U.S. Pat. No. 4,440,871. Other suitable molecular sieves can be selected from chromosilicates; gallium silicates; iron silicates; aluminum phosphates (ALPO), such as ALPO-11 described in U.S. Pat. No. 4,310,440; titanium aluminosilicates (TASO), such as TASO-45 described in EP-A No. 229,295; boron silicates, described in U.S. Pat. No. 4,254,297; titanium aluminophosphates (TAPO), such as TAPO-11 described in U.S. Pat. No. 4,500,651; and iron aluminosilicates.

The cracking catalyst comprising at least one molecular sieve is also meant to encompass "crystalline admixtures" which are thought to be the result of faults occurring within the crystal or crystalline area during the synthesis of the zeolites. Examples of crystalline admixtures of ZSM-5 and ZSM-11 are disclosed in U.S. Pat. No. 4,229,424 which is incorporated herein by reference. The crytalline admixtures are themselves medium pore size zeolites and are not to be confused with physical admixtures of zeolites in which distinct crystals of crystallites of different zeolites are physically present in the same catalyst composite or hydrothermal reaction mixtures.

The cracking catalysts of the present invention are held together with an inorganic oxide matrix component. The inorganic oxide matrix component binds the catalyst components together so that the catalyst particles are hard enough to survive interparticle and reactor wall collisions. The inorganic oxide matrix can be made from an inorganic oxide sol or gel which is dried to "glue" the catalyst components together. Preferably, the inorganic oxide matrix is not catalytically active and will be comprised of oxides of silicon and aluminum. It is also preferred that separate alumina phases be incorporated into the inorganic oxide matrix. Species of aluminum oxyhydroxides-g-alumina, boehmite, diaspore, and transitional aluminas such as a-alumina, b-alumina, g-alumina, d-alumina, c-alumina, k-alumina, and r-alumina can be employed. Preferably, the alumina species is an aluminum trihydroxide such as gibbsite, bayerite, nordstrandite, or doyelite. The matrix material may also contain phosphorous or aluminum phosphate.

EXAMPLES

The invention will now be further understood by reference to the following examples.

Example 1

A light cat naphtha was distilled into five different fractions to study feedstock effects in naphtha cracking. The distillation was performed according to the ASTM specification for distillation of naphtha, ASTM D-86. The results of the feedstock component properties of the distilled light cat naphtha are given in Table 1.

TABLE 1

FEED COMPONENT PROPERTIES

| | Feed | | | | | *** LCN *** | |
|---|---|---|---|---|---|---|---|
| | IBP-130 | 130-150 | 150-170 | 170-190 | 190+ | Wt. Avg. | Actual |
| | | | % of Feed | | | | |
| | 33.1 | 14.3 | 11.9 | 7.3 | 33.4 | | |
| Olefins, Wt. % | | | | | | | |
| C5 | 62.4 | 9.2 | 0.3 | 0.0 | 0.0 | 22.0 | 26.2 |
| C6 | 4.4 | 49.0 | 48.4 | 20.8 | 0.6 | 16.0 | 15.8 |
| C7 | 0.1 | 5.2 | 14.3 | 30.5 | 22.0 | 12.1 | 10.6 |
| C8 | 0.0 | 0.0 | 0.0 | 0.0 | 5.4 | 1.8 | 1.3 |
| C9 | 0.0 | 0.0 | 0.0 | 0.0 | 1.2 | 0.4 | 0.1 |
| C10 | 0.0 | 0.0 | 0.0 | 0.0 | 0.1 | 0.0 | 0.0 |
| C11 | 0.0 | 0.0 | 0.0 | 0.0 | 0.0 | 0.0 | 0.0 |
| C12 | 0.0 | 0.0 | 0.0 | 0.0 | 0.0 | 0.0 | 0.0 |
| Total, % | 66.9 | 63.5 | 63.0 | 51.3 | 29.4 | 52.3 | 54.0 |

LCN distilled into five cuts to study feedstock effects in naphtha cracking
IBP-130° F. cut olefins mostly pentenes
130-150/150-170° F. cut olefins mostly hexenes
190° F.+ mostly heptenes LCN distilled into five cuts to study feedstock effects in naphtha cracking
  IBP-130° F. cut olefins mostly hexens
  130-150/150-170°F. cut olefins mostly hexenes
  190°F.+ mostly heptenes

Example 2

A series of tests in a small bench reactor were conducted on the various boiling fractions of the light cat naphtha. All tests were conducted at 575° C., 72 hr$^1$ WHSV over a fixed bed of 0.3 g of ZSM-5 medium-pore zeolite catalyst. Prior to the cracking tests, the ZSM-5 catalyst was aged by steaming it with 100% steam at 816° C. and 1 atmosphere for 16 hours.

The yields of key products from these series of tests are given in Table 2.

TABLE 2

OLEFINSMAX IN LCN CRACKING

| | | | | | | *** LCN *** | |
|---|---|---|---|---|---|---|---|
| Feed | IBP-130 | 130-150 | 150-170 | 170-190 | 190+ | Wt. Avg. | Actual |
| C4-Conv., Wt % | 22.4 | 41.4 | 45.0 | 39.9 | 32.3 | 32.3 | 32.8 |
| Key Yields, Wt % | | | | | | | |
| Ethylene | 3.3 | 3.0 | 3.5 | 2.2 | 2.6 | 3.0 | 2.7 |
| Propylene | 10.8 | 27.5 | 27.8 | 21.0 | 15.4 | 17.4 | 16.9 |
| Butylene | 7.6 | 10.0 | 12.4 | 15.5 | 12.2 | 10.6 | 11.6 |
| Lt Sats | 0.8 | 0.9 | 1.4 | 1.1 | 2.1 | 1.3 | 1.7 |
| Propane | 0.1 | 0.4 | 0.5 | 0.4 | 0.4 | 0.3 | 0.4 |
| C3=/C4-Sel | 48.2 | 66.4 | 61.8 | 52.6 | 47.7 | 53.9 | 51.5 |

C6 cuts (130-150° F. and 150-170° F.) show the highest propylene yield with OlefinsMax cracking catalyst The effluent stream of the reactor was analyzed by on-line gas chromatography ("GC"). A column having a length of 60 m packed with fused silica was used for the analysis. The GC used was a dual FID Hewlett-Packard Model 5880.

Example 3

In addition to ZSM-5, the various boiling fractions of the light cat naphtha were also tested with a SAPO-11 catalyst. In the case of SAPO-11, the zeolite was tested fresh. Otherwise, the procedure used in the experiments with SAPO-11 was nominally identical to the experiments with ZSM-5. The results are given in Table 3.

TABLE 3

SAPO-11 IN LCN CRACKING

| Feed | IBP-130 | 130-150 | 150-170 | 170-190 | 190+ | *** LCN *** Wt. Avg. | Actual |
|---|---|---|---|---|---|---|---|
| C4-Conv., Wt % | 17.3 | 41.4 | 33.0 | 30.2 | 24.6 | 26.0 | 26.5 |
| Key Yields, Wt % | | | | | | | |
| Ethylene | 3.7 | 1.5 | 1.1 | 0.9 | 0.9 | 1.9 | 1.9 |
| Propylene | 10.5 | 35.8 | 26.5 | 17.0 | 10.4 | 16.4 | 15.2 |
| Butylene | 2.6 | 3.3 | 4.4 | 11.0 | 11.8 | 6.6 | 7.4 |
| Lt Sats | 0.5 | 0.9 | 1.0 | 1.2 | 1.5 | 1.0 | 2.1 |
| Propane | 0.1 | 0.3 | 0.2 | 0.3 | 0.4 | 0.2 | 0.3 |
| C3=/C4-Sel | 60.7 | 86.5 | 80.3 | 56.3 | 42.3 | 63.1 | 57.4 |

C6 cuts (130-150° F. and 150-170° F.) also show the highest propylene yield with SAPO-11

The invention claimed is:

1. A process for producing increased amounts of propylene from naphtha-boiling-range feedstreams in a process unit comprising at least a reaction zone, a stripping zone, a regenerator zone, and at least one fractionation zone, which process comprises:
   (a) fractionating said naphtha-boiling-range feedstream to produce a $C_6$-rich fraction and a $C_6$-lean fraction, wherein the $C_6$-rich fraction contains at least 50 wt % $C_6$ compounds;
   (b) injecting at least a portion of said $C_6$-lean fraction into the reaction zone, said reaction zone containing a cracking catalyst comprising at least one molecular sieve having an average pore diameter of less than about 0.7 nm wherein said $C_6$-lean fraction contacts said zeolite cracking catalyst under effective conditions thereby resulting in at least spent catalyst particles having carbon deposited thereon and a product stream;
   (c) injecting at least a portion of said $C_6$-rich fraction at a place in the process unit selected from: i) downstream of the $C_6$-lean fraction; ii) the stripping zone; and iii) a dilute phase above the stripping zone;
   (d) contacting at least a portion of said spent catalyst particles with a stripping gas in the stripping zone under conditions effective at removing at least a portion of any volatiles therefrom thereby resulting in at least stripped spent catalyst particles;
   (e) regenerating at least a portion of said stripped spent catalysts in a regeneration zone in the presence of an oxygen-containing gas under conditions effective at burning off at least a portion of said carbon deposited thereon thereby producing at least regenerated catalyst particles;
   (f) recycling at least a portion of said regenerated catalyst particles to said reaction zone;
   (g) fractionating at least a portion of said product stream of step (b) to produce at least a fraction rich in propylene; and
   (h) collecting at least a portion of the fraction rich in propylene.

2. The process of claim 1 wherein the at least one molecular sieve is selected from zeolites and silicoaluminophosphates.

3. The process of claim 2 wherein the at least one molecular sieve is a medium-pore zeolite.

4. The process of claim 3 wherein the medium-pore zeolite is selected from the group consisting of ZSM-5, ZSM-11, ZSM-12, ZSM-22, ZSM-23, ZSM-48, and ZSM-50.

5. The process of claim 2 wherein the silicoaluminophosphates is selected from the group consisting of SAPO-11, SAPO-34, SAPO-41, and SAPO-42.

6. The process of claim 1 wherein the propylene rich fraction has a propylene concentration greater than about 60 wt %.

7. The process of claim 1 wherein said effective conditions in the reaction zone include temperatures from about 500° C. to about 650° C.

8. The process according to claim 1 wherein said reaction zone comprises at least one catalyst bed selected from dynamic catalyst beds.

9. The process according to claim 8 wherein said dynamic catalyst bed is selected from fluidized, slurried and ebullating catalyst beds.

10. The process according to claim 1 wherein said molecular sieve comprises about 10 wt. % to about 50 wt. % of the total fluidized catalyst composition.

11. The process according to claim 1 wherein said molecular sieve is selected from chromosilicates, gallium silicates, iron silicates, aluminum phosphates (ALPO), titanium aluminosilicates (TASO), boron silicates, titanium aluminophosphates (TAPO), and iron aluminosilicates.

12. The process of claim 1 wherein said cracking catalyst further comprises an inorganic oxide matrix component.

13. The process of claim 12 wherein said inorganic oxide matrix component is not catalytically active and is selected from oxides of silicon and aluminum.

14. A process for producing increased amounts of propylene from naphtha-boiling-range feedstreams in a process unit comprising at least a reaction zone, a stripping zone, a regenerator zone, and at least one fractionation zone, which process comprises:
   (a) injecting a naphtha-boiling-range feedstream into the reaction zone, said reaction zone containing a cracking catalyst comprising at least one molecular sieve having an average pore diameter of less than about 0.7 nm wherein said naphtha-boiling-range feedstream contacts said cracking catalyst under effective conditions thereby resulting in at least spent catalyst particles having carbon deposited thereon and a product stream;
   (b) contacting at least a portion of said spent catalyst particles with a stripping gas in the stripping zone under conditions effective at removing at least a portion of any volatiles therefrom thereby resulting in at least stripped spent catalyst particles;
   (c) regenerating at least a portion of said stripped spent catalysts in a regeneration zone in the presence of an oxygen-containing gas under conditions effective at to burning off at least a portion of said carbon deposited thereon thereby producing at least regenerated catalyst particles;

(d) recycling at least a portion of said regenerated catalyst particles to said reaction zone;

(e) fractionating at least a portion of said product stream of step (a) to produce at least a fraction rich in propylene, a $C_6$-rich fraction, and a $C_6$-lean fraction, wherein the $C_6$ fraction contains at least 50 wt % $C_6$ compounds; and (f) collecting at least a portion of the fraction rich in propylene and the $C_6$-lean fraction and recycling at least a portion of the $C_6$-rich fraction to a place in the process unit selected from: i) downstream of the $C_6$-lean fraction; ii) the stripping zone; iii) with the $C_6$-lean fraction; and iv) a dilute phase above the stripping zone.

15. The process of claim 14 wherein the at least one molecular sieve is selected from zeolites and silicoaluminophosphates.

16. The process of claim 15 wherein the at least one molecular sieve is a medium-pore zeolite.

17. The process of claim 16 wherein the medium-pore zeolite is selected from the group consisting of ZSM-5, ZSM-11, ZSM-12, ZSM-22, ZSM-23, ZSM-48, and ZSM-50.

18. The process of claim 15 wherein the silicoaluminophosphates is selected from the group consisting of SAPO-11, SAPO-34, SAPO-41, and SAP0-42.

19. The process of claim 13 wherein the propylene rich fraction has a propylene concentration greater than about 60 wt %.

20. The process of claim 13 wherein said effective conditions in the reaction zone include temperatures from about 500° C. to about 650° C.

21. The process according to claim 14 wherein said reaction zone comprises at least one catalyst bed selected from dynamic catalyst beds.

22. The process according to claim 21 wherein said dynamic catalyst bed is selected from fluidized, slurried and ebullating catalyst beds.

23. The process according to claim 14 wherein said molecular sieve comprises about 10 wt. % to about 50 wt. % of the total fluidized catalyst composition.

24. The process according to claim 14 wherein said molecular sieve is selected from chromosilicates, gallium silicates, iron silicates, aluminum phosphates (ALPO), titanium aluminosilicates (TASO), boron silicates, titanium aluminophosphates (TAPO), and iron aluminosilicates.

25. The process of claim 14 wherein said cracking catalyst further comprises an inorganic oxide matrix component.

26. The process of claim 25 wherein said inorganic oxide matrix component is not catalytically active and is selected from oxides of silicon and aluminum.

27. A process for producing increased amounts of propylene from naphtha-boiling-range feedstreams in a process unit comprising at least a reaction zone, a stripping zone, a regenerator zone, and at least one fractionation zone, which process comprises:

(a) fractionating said naphtha-boiling-range feedstream to produce a $C_6$-rich feed fraction, wherein the $C_6$-rich feed fraction contains at least 50 wt % $C_6$ compounds and a $C_6$-lean feed fraction;

(b) injecting at least a portion of said $C_6$-lean feed fraction into the reaction zone, said reaction zone containing a cracking catalyst comprising at least one molecular sieve having an average pore diameter of less than about 0.7 nm wherein said $C_6$-lean feed fraction contacts said cracking catalyst under effective conditions thereby resulting in at least spent catalyst particles having carbon deposited thereon and a product stream;

(c) injecting at least a portion of said $C_6$-rich feed fraction at a place in the process unit selected from: i) downstream of the $C_6$-lean fraction; ii) the stripping zone; and iii) a dilute phase above the stripping zone;

(d) contacting at least a portion of said spent catalyst particles with a stripping gas in the stripping zone under conditions effective at removing at least a portion of any volatiles therefrom thereby resulting in at least stripped spent catalyst particles;

(e) regenerating at least a portion of said stripped spent catalysts in a regeneration zone in the presence of an oxygen-containing gas, said regeneration zone operated under conditions effective at burning-off at least a portion of said carbon deposited thereon thereby producing at least regenerated catalyst particles;

(f) recycling at least a portion of said regenerated catalyst particles to said reaction zone;

(g) fractionating at least a portion of said product stream of step (b) to produce at least a fraction rich in propylene; a $C_6$-rich product fractions, wherein the $C_6$-rich product fraction contains at least 50 wt % $C_6$ compounds, and $C_6$-lean product fraction; and (h) collecting at least a portion of the propylene and $C_6$-lean product fraction and recycling at least a portion of the $C_6$-rich product fraction to a place in the process unit selected from: i) downstream the $C_6$-lean feed fraction; ii) the stripping zone; and iii) a dilute phase above the stripping zone.

28. The process of claim 27 wherein the at least one molecular sieve is selected from zeolites and silicoaluminophosphates.

29. The process of claim 27 wherein the at least one molecular sieve is a medium-pore zeolite.

30. The process of claim 29 wherein the medium-pore zeolite is selected from the group consisting of ZSM-5, ZSM-11, ZSM-12, ZSM-22, ZSM-23, ZSM-48, and ZSM-50.

31. The process of claim 28 wherein the silicoaluminophosphates is selected from the group consisting of SAPO-11, SAPO-34, SAPO-41, and SAPO-42.

32. The process of claim 27 wherein the propylene rich fraction has a propylene concentration greater than about 60 wt %.

33. The process of claim 27 wherein said effective conditions in the reaction zone include temperatures from about 500° C. to about 650° C.

34. The process according to claim 27 wherein said reaction zone comprises at least one catalyst bed selected from dynamic catalyst beds.

35. The process according to claim 34 wherein said dynamic catalyst bed is selected from fluidized, slurried and ebullating catalyst beds.

36. The process according to claim 27 wherein said molecular sieve comprises about 10 wt. % to about 50 wt. % of the total fluidized catalyst composition.

37. The process according to claim 27 wherein said molecular sieve is selected from chromosilicates, gallium silicates, iron silicates, aluminum phosphates (ALPO), titanium aluminosilicates (TASO), boron silicates, titanium aluminophosphates (TAPO), and iron aluminosilicates.

38. The process of claim 27 wherein said cracking catalyst further comprises an inorganic oxide matrix component.

39. The process of claim 38 wherein said inorganic oxide matrix component is not catalytically active and is selected from oxides of silicon and aluminum.

* * * * *